(12) United States Patent
Cantor et al.

(10) Patent No.: US 7,655,399 B2
(45) Date of Patent: Feb. 2, 2010

(54) METHODS FOR PRENATAL DIAGNOSIS OF CHROMOSOMAL ABNORMALITIES

(75) Inventors: Charles R Cantor, Del Mar, CA (US); Chunming Ding, Shatin (CN)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 10/575,119

(22) PCT Filed: Oct. 8, 2004

(86) PCT No.: PCT/US2004/033175

§ 371 (c)(1),
(2), (4) Date: May 16, 2006

(87) PCT Pub. No.: WO2005/035725

PCT Pub. Date: Apr. 21, 2005

(65) Prior Publication Data

US 2007/0059707 A1    Mar. 15, 2007

Related U.S. Application Data

(60) Provisional application No. 60/509,775, filed on Oct. 8, 2003.

(51) Int. Cl.
C12Q 1/68 (2006.01)
(52) U.S. Cl. ........................................................ 435/6
(58) Field of Classification Search ...................... None
See application file for complete search history.

(56) References Cited

U.S. PATENT DOCUMENTS

| | | | |
|---|---|---|---|
| 4,874,693 A | 10/1989 | Bogart | |
| 5,436,142 A | 7/1995 | Wigler et al. | |
| 5,786,146 A | 7/1998 | Herman et al. | |
| 5,871,917 A | 2/1999 | Duffy | |
| 6,136,530 A | 10/2000 | Produslo | |
| 6,331,393 B1 | 12/2001 | Laird et al. | |
| 6,927,028 B2 * | 8/2005 | Dennis et al. ................ | 435/6 |
| 6,977,162 B2 | 12/2005 | Dhallan | |
| 7,208,274 B2 | 4/2007 | Dhallan | |
| 7,332,277 B2 | 2/2008 | Dhallan | |
| 7,348,139 B1 * | 3/2008 | Herman et al. .............. | 435/6 |
| 7,442,506 B2 | 10/2008 | Dhallan | |
| 2002/0025532 A1 | 2/2002 | Huang | |
| 2002/0155451 A1 | 10/2002 | Makrigiorgos | |
| 2003/0017487 A1 | 1/2003 | Xue | |
| 2003/0022215 A1 | 1/2003 | Makrigiorgos | |
| 2003/0099997 A1 | 5/2003 | Bestor | |
| 2004/0081993 A1 | 4/2004 | Cantor | |
| 2004/0224331 A1 | 11/2004 | Cantor | |
| 2006/0121452 A1 | 6/2006 | Dhallan | |
| 2007/0122805 A1 | 5/2007 | Cantor | |
| 2007/0122835 A1 | 5/2007 | Dhallan | |
| 2007/0207466 A1 | 9/2007 | Cantor | |

FOREIGN PATENT DOCUMENTS

| | | |
|---|---|---|
| WO | 00/50869 A2 | 8/2000 |
| WO | 01/42496 A2 | 6/2001 |
| WO | 01/68913 | 9/2001 |
| WO | 01/90399 A2 | 11/2001 |
| WO | 01/96607 A2 | 12/2001 |

OTHER PUBLICATIONS

Buchanan, F.C. et al., "Association of a missense mutation in the bovine leptin gene with carcass fat content and leptin MRNA levels," Genetics Selection Evolution, EDP Sciences, Les Ulis., FR 34(1):105-116, 2002.
Saito et al., "Prenatal DNA diagnosis of a single-gene disorder from maternal plasma," The Lancet, Lancet Limited London, GB 356(9236):1170, 2000.
Ahmed et al., "Prenatal diagnosis of beta-thalassaemia in Pakistan: experience in a Muslim country" Prenatal Diagn 20(5):378-383, 2000.
Amicucci, P. et al., "Prenatal diagnosis of myotonic dystrophy using fetal DNA obtained from maternal plasma." Clinical Chemistry 46(2):301-302, 2000.
Böcker, "SNP and mutation discover using base-specific cleavage and MALDI-TOF mass spectrometry." Bioinformatics 19(Suppl 1):i44-i53, 2003.
Braun et al., "Improved Analysis of Microsatellites Using Mass Spectrometry." Genomics 46:18-23, 1997.
Cheung, M. C. et al., "Prenatal diagnosis of sickle cell anaemia and thalassaemia by analysis of fetal cells in maternal blood." Nat Genet 14:264-268, 1996.
Chiu, R. W. K. and Lo, Y. M. D., "Application of fetal DNA in maternal plasma for noninvasive prenatal diagnosis." Expert Rev Mol Diagn 2:32-40, 2002.
Chiu, R. W. K. et al., "Noninvasive prenatal exclusion of congenital adrenal hyperplasia by maternal plasma analysis: a feasibility study." Clin Chem 48:778-780, 2002.
Chiu, R. W. K. et al., "Prenatal exclusion of beta thalassaemia major by examination of maternal plasma." The Lancet 360:998-1000, 2002.
Clark, A. G. et al., "Inference of haplotypes from PCR-amplified samples of diploid populations." Mol Biol Evol 7 (2):111-122, 1990.
Costa, J. M. et al., "New strategy for prenatal diagnosis of X-linked disorders." N Engl J Med 346:1502, 2002.
Costa, J. M. et al., "First-trimester fetal sex determination in maternal serum using real-time PCR." Prenatal Diagn 21:1070-1074, 2001.

(Continued)

Primary Examiner—Misook Yu
(74) Attorney, Agent, or Firm—Nixon Peabody LLP

(57) ABSTRACT

Chromosomal abnormalities are responsible for a significant number of birth defects, including mental retardation. The present invention is related to methods for non-invasive and rapid, prenatal diagnosis of chromosomal abnormalities based on analysis of a maternal blood sample. The invention exploits the differences in DNA between the mother and fetus, for instance differences in their methylation states, as a means to enrich for fetal DNA in maternal plasma sample. The methods described herein can be used to detect chromosomal DNA deletions and duplications. In a preferred embodiment, the methods are used to diagnose chromosomal aneuploidy and related disorders, such as Down's and Turner's Syndrome.

13 Claims, No Drawings

OTHER PUBLICATIONS

Daly, M. J. et al., "High-resolution haplotype structure in the human genome." Nat Genet 29:229-232, 2001.

Ding and Cantor, "Direct molecular haplotyping of long-range genomic DNA with M1-PCR." PNAS 100 (13):7449-7453, 2003.

Doris et al., "Quantitative analysis of gene expression by ion-pair high-performance liquid chromatography." J Chromatography A 806(1):47-60, 1998.

Douglas, J. A. et al., "Experimentally-derived haplotypes substantially increase the efficiency of linkage disequilibrium studies." Nat Genet 28:361-364, 2001.

Drysdale et al., "Complex promoter and coding region beta 2-adrenergic receptor haplotypes alter receptor expression and predict in vivo responsiveness." PNAS 97(19):104483-10488, 2000.

Elso et al., "Mutation Detection Using Mass Spectrometric Separation of Tiny Oligonucleotide Fragments." Genome Research 12:1428-1433, 2002.

Finning, K. M. et al., "Prediction of fetal D status from maternal plasma: introduction of a new noninvasive fetal RHD genotyping service." Transfusion 42:1079-1085, 2002.

Fucharoen, G. et al., "Prenatal detection of fetal hemoglobin E gene from maternal plasma." Prenatal Diagn. 23:393-396, 2003.

Furlong, R. A. et al., "Analysis of four microsatellite markers on the long arm of chromosome 9 by meiotic recombination in flow-sorted single sperm." Am J Hum Genet 52(6):1191-1199, 1993.

Gabriel, S. B. et al., "The structure of haplotype blocks in the human genome." Science 296:2225-2229, 2002.

González-González M. C. et al., "Early Huntington disease prenatal diagnosis by maternal semiquantitative fluorescent-PCR." Neurology 60:1214-1215, 2003.

González-González M. C. et al., "Prenatal detection of a cystic fibrosis mutation in fetal DNA from maternal plasma." Prenatal Diagn 22(10):946-948, 2002.

Heid et al., "Real time quantitative PCR." Genome Res 6(10):986-994, 1996.

Hodge et al., "Loss of information due to ambiguous haplotyping of SNPs." Nature Genet 21(4):360-361, 1999.

Jacquy et al., "A quantitative study of peripheral blood stem cell contamination in diffuse large-cell non-Hodgkin's lymphoma: one-half of patients significantly mobilize malignant cells." Br J Haematology 110(3):631-637, 2000.

Jeffreys et al., "Amplification of human minisatellites by the polymerase chain reaction: towards DNA fingerprinting of single cells." Nucleic Acids Res 16(23):10953-10971, 1988.

Jeffreys et al., "Repeat unit sequence variation in minisatellites: a novel source of DNA polymorphism for studying variation and mutation by single molecule analysis." Cell 60(3):473-485, 1990.

Judson, R. et al., "The predictive power of haplotypes in clinical response." Pharmacogenomics 1(1):15-26, 2000.

Krebs et al., "Genotyping of dinucleotide tandem repeats by MALDI mass spectrometry of ribozyme-cleaved RNA transcripts." Nature Biotechnology 19:877-880, 2001.

Lo, Y. M. et al., "Quantitative analysis of fetal DNA in maternal plasma and serum: implications for noninvasive prenatal diagnosis." Am J Hum Genet 62:768-775, 1998.

Lo, Y. M. et al., "Presence of fetal DNA in maternal plasma and serum." Lancet 350(9076):485-487, 1997.

Lo, Y. M. Dennis et al., "Prenatal diagnosis of fetal RhD status by molecular analysis of maternal plasma." N Engl J Med 339:1734-1738, 1998.

Lo, Y. M., "Detection of minority nucleic acid populations by PCR." J Pathol 174:1-6, 1994.

Nasis, O. et al. "Improvement in sensitivity of allele-specific PCR facilitates reliable noninvasive prenatal detection of cystic fibrosis." Clin Chem 50:694-701, 2004.

Rijnders, R. J. et al., "Clinical applications of cell-free fetal DNA from maternal plasma." Obstet Gynecol 103:157-164, 2004.

Sekizawa, A. et al., "Accuracy of fetal gender determination by analysis of DNA in maternal plasma." Clin Chem 47(10):1856-1858, 2001.

Suomalainen, A. and Syvänen, A. C., "Quantitative analysis of human DNA sequences by PCR and solid-phase minisequencing." Mol Biotechnol 15(2):123-131, 2000.

Tang, et al., "Single nucleotide polymorphism analyses by MALDI-TOF MS." International Journal of Mass Spectrometry 226:37-54, 2003.

* cited by examiner

METHODS FOR PRENATAL DIAGNOSIS OF CHROMOSOMAL ABNORMALITIES

CROSS-REFERENCE TO RELATED APPLICATIONS

This application is a 371 National Phase Entry Application of co-pending International Application PCT/US2004/033175, filed Oct. 8, 2004, which designated the U.S. and claims benefit under 35 U.S.C §119(e) of U.S. Provisional Application No. 60/509,775, filed Oct. 8, 2003; the contents of which are herewith incorporated by reference in their entirety.

FIELD OF THE INVENTION

The present invention is related to methods for non-invasive, prenatal diagnosis of chromosomal abnormalities. The methods of the invention can be used to detect chromosomal DNA deletions and duplications. In a preferred embodiment, the methods are used to diagnose chromosomal aneuploidy and related disorders, such as Down's and Turner's Syndrome. The present invention further provides for methods of identifying methyl-polymorphic probes that can be used for the detection of fetal chromosome abnormalities.

BACKGROUND OF THE INVENTION

Chromosomal abnormalities are responsible for a significant number of birth defects, including mental retardation. Abnormalities can appear in the form of chromosomal DNA duplications and deletions, as well in the form as chromosomal aneuploidy, which is the abnormal presence or absence of an entire chromosome. Conditions where an organism has less than, or more than the normal diploid number of chromosomes give rise to a multitude of abnormal characteristics and are responsible for many syndromes. Down's syndrome, or trisomy 21, is the most common example of a chromosomal aneuploidy and involves an extra chromosome 21. Other common chromosomal aneuploidies are trisomy 13, trisomy 18, Turner's syndrome and Klinefelter's syndrome.

The options for the prenatal detection of chromosomal abnormalities are mainly limited to invasive methods with a small but finite risk for fetal loss. The most common method for detection of abnormalities is amniocentesis. However, because amniocentisis is an invasive method it is generally performed only on older mothers where the risk of a fetus presenting with chromosomal abnormalities is increased. It would therefore be beneficial to establish non-invasive methods for the diagnosis of fetal chromosomal abnormalities that can be used on larger population of prospective mothers. One such non-invasive method has been described in U.S. Pat. No. 4,874,693, which discloses a method for detecting placental dysfunction indicative of chromosomal abnormalities by monitoring the maternal levels of human chorionic gonadotropin hormone (HCG). However, while this method is non-invasive and can be used to screen prospective mothers of all ages, it does not serve as a diagnostic of the particular chromosomal abnormality present, nor is a guarantee of its presence.

In addition to being invasive at the sample taking step, the existing prenatal diagnosis methods are also time consuming to perform. For example, Geisma-staining is the technique most widely used and requires that the cells be in metaphase or dividing, when the test is preformed. Each chromosome pair stains in a characteristic pattern of light and dark bands. Using this method all of the chromosomes can be individually distinguished and readily reveal the nature of any structural or numerical abnormalities. Geisma-staining does not always detect subtle chromosomal rearrangements. If chromosomal rearrangements are suspected and not detected using this method, further detailed analysis can be done using fluorescent in situ hybridization (FISH) or spectral karyotyping (SKY). Tests results using Geisma-staining can take one to two weeks.

SKY is a technique that paints each of the metaphase chromosomes with a different probe (dye color). Because each chromosome-specific probe emits its own signature wavelength of fluorescence, structural rearrangement are easily seen, and the chromosomes involved can be readily identified. SKY requires that cells be in metaphase therefore results can take one to two weeks.

FISH is a technique that uses a fluorescent probe (dye) that attaches, or hybridizes, to specific individual chromosomes or certain regions of chromosomes. The affected chromosomes or regions fluoresce, or signal, their presence, or lack of, and can be visually analyzed through a fluorescent microscope. FISH is used to identify particular chromosomal rearrangements or rapidly diagnose the existence of an abnormal number of chromosomes. FISH is currently the most rapid diagnosis method of abnormal chromosome numbers. The speed is possible because cells do not need to be in metaphase in order to do the analysis. Results of the test are typically known in two to three days Thus, there is a need in the art for non-invasive prenatal diagnostic methods that can rapidly and accurately help determine the presence and the type of chromosomal aberrations.

SUMMARY OF THE INVENTION

The present invention describes a method for non-invasive prenatal diagnosis of chromosomal abnormalities, such as chromosomal aneuploidy, and allows rapid production of accurate results. The methods of the invention use plasma samples obtained from a pregnant female. It has been shown that maternal samples contain a small percentage of fetal DNA but the percentage of the fetal cells present in the maternal plasma is small.

The autosomal chromosomes have one allele inherited from the mother (A, as shown in the table below) and one allele from the father (B as shown in the table below). In a situation, wherein fetal DNA represents about 2% of the total DNA present in the maternal plasma sample, the presence of fetal alleles can be presented as follows:

|  | Maternal DNA (98%) | Fetal DNA (2%) | B % |
|---|---|---|---|
| Trisomy of maternally inherited allele (A) | AA | AAB | 2/202 |
| Normal | AA | AB | 2/200 |

Thus, because the difference of B % between normal and trisomy is only (2/200-2/202) or 0.01%, the difference is too small to detect using even the best available quantification methods.

The present invention solves this problem by enriching, relatively, the amount of fetal DNA in the maternal plasma sample before detecting the alleles present in the sample. To enrich for fetal DNA present in plasma of the mother to allow accurate detection of fetal alleles present in the sample, the invention exploits differences in the DNA between the mother and fetus, for instance, differences in the DNA methylation states. Thus, the maternal DNA can be substantially reduced, masked, or destroyed completely, and the sample is left with DNA majority of which is of fetal origin. The selective destruction of maternal DNA can be performed using one or more enzymes, such as methylation sensitive enzymes, which selectively digest maternal nucleic acids around the region, which is later used for detection of the allele frequency. The allele frequency of fetal DNA is then determined using polymorphic markers adjacent to the selected chromosomal regions. A difference in allele frequency as compared to a control sample is indicative of a chromosomal abnormality.

In one embodiment, a method for detecting a chromosomal abnormality is provided that comprises: a) obtaining a plasma sample from a pregnant female, b) optionally isolating DNA from the said plasma sample, c) digesting the DNA with an enzyme, such as a methyl-sensitive enzyme, that selectively digests the maternal or fetal DNA, d) using the selective digestion to obtain a DNA sample enriched for fetal or maternal DNA, e) determining the maternal or paternal allele frequency using polymorphic markers adjacent to the selected fetal DNA regions, and f) comparing the paternal or maternal allele frequency of step e) to a control DNA sample, wherein a difference in allele frequency is indicative of a chromosomal abnormality. Preferably, one would also compare the putative abnormal DNA against a panel of normal DNA and/or abnormal DNA to take polymorphic differences into account.

Thus, if the maternal DNA is completely destroyed by digestion, the fetal allele frequency can be detected as shown in the table below:

|  | Maternal DNA in plasma sample (digested, 0%) | Fetal DNA (100% in the plasma sample) | B % |
|---|---|---|---|
| Trisomy of maternally inherited allele | AA | AAB | ⅓ (or 33.3%) |
| Normal | AA | AB | ½ (or 50%) |

The relative enrichment of the fetal DNA in the maternal plasma sample now allows accurate detection of allele frequencies using practically any method of nucleic acid detection. The ratio between the maternal and paternal allele in the maternal plasma sample thus reflects the allelic ratio in the fetus only. Therefore, if more than two maternal alleles are present in the sample, the ratio will be significantly altered from the normal ½.

Any differences between the fetal and maternal DNA can be exploited, for example exploitation of Y-chromosome specific DNA and telomere length. Differences in DNA between mother and fetus can be determined by known means. In the case where the difference is differential methylation, methyl-sensitive enzymes digest unmethylated maternal DNA that is methylated in the fetus, or vise versa. For instance, when the fetal DNA region is methylated, methyl-sensitive enzymes are used to digest unmethylated maternal DNA. The digestion leaves only methylated fetal DNA fragments, thereby enriching for fetal DNA. Polymorphic markers that are close to or within the differentially methylated DNA regions are then used as labels to detect the frequency of maternal or paternal DNA in the maternal plasma sample. The allele frequency of the maternal and paternal DNA is compared to the allele frequency that is normally observed in genomic DNA obtained from a healthy individual that does not have a chromosome abnormality. In this manner, any chromosomal abnormalities can be detected. One or more alleles can be detected simultaneously, thus allowing screening of several chromosomal abnormalities simultaneously from the same sample. Alternatively, enzymes that digest only methylated DNA can be used to enrich for DNA that is unmethylated in the fetus but methylated in the mother. The methods of the present invention are suitable to detect chromosomal DNA duplications, or deletions, and to detect chromosomal aneuploidy.

While it is preferred that the first step destroys the maternal alleles substantially completely, this is not necessary. The present invention also provides a method, wherein, if the maternal DNA is not completely destroyed, a control allele is used from one or more chromosomes that are not expected to be present in duplicate. The situation can be presented as follows:

|  | Maternal DNA | Fetal DNA | B (or D) % 100% digestion | B (or D) % 98% digestion |
|---|---|---|---|---|
| Trisomy | AA | AAB | 33.3% | 20% |
| Non-aneuploidy | CC | CD | 50% | 25% |

In the table, the alleles B and D are paternally inherited alleles present in the fetal DNA.

Alternatively, fetal DNA can be amplified further after the first digestion. Thus, the invention provides a method, wherein after the initial digestion of maternal DNA, the sample is amplified using an amplification method which selectively amplifies the fetal DNA. Alternatively, one preserves the differences, for example the methylation differences, between the maternal and fetal DNA. The amplified sample is consequently digested again thus allowing a larger percentage of fetal DNA to be achieved. The digestion/amplification scheme can be performed, of course, more than once, if desired. Amplification step can also be used together with a detection of a control allele.

Therefore, in one embodiment, the methods of the present invention further comprise an amplification scheme to enrich for fetal DNA. In one aspect, the amplification method comprises a) obtaining a plasma sample from a pregnant female and optionally isolating DNA from said sample, b) digesting isolated DNA with a methyl-sensitive enzyme that digests only unmethylated DNA, c) isolating undigested DNA from step b, d) amplifying the undigested DNA from step c while simultaneously using a DNA methylase to methylate nascent hemi-methylated DNA, e) digesting amplified DNA of step c with an enzyme that digests only unmethylated DNA, f) determining the maternal or paternal allele frequency using, for example, polymorphic markers adjacent to methylated fetal DNA regions and, g) comparing the paternal or maternal allele frequency of step f) to a control DNA sample, wherein a difference allele frequency is indicative of a chromosomal abnormality.

In another embodiment, the invention provides a method for the diagnosis of trisomy 21 (Down's syndrome). The method comprises: a) obtaining a plasma sample from a pregnant female, b) optionally isolating DNA from said plasma sample, c) digesting the DNA with an enzyme, such as a methyl-sensitive enzyme, that digests only maternal or fetal DNA, d) determining the paternal allele frequency using polymorphic markers adjacent to the selected fetal DNA regions of chromosome 21, and e) comparing the paternal allele frequency of step d to a control DNA sample, wherein a paternal allele frequency less than the control is indicative of Downs's syndrome.

In another embodiment, the invention provides a kit for detecting chromosomal aneuploidy in the maternal plasma sample, wherein the kit comprises one or more enzymes to specifically digest the maternal DNA in the plasma sample of a pregnant female, and primers to detect paternal and maternal allele frequency of polymorphic markers in the enriched fetal DNA regions in order to detect chromosomal deletions, insertions or aneuploidy. The kit may also comprise containers, enzymes, such as polymerases, and buffers to facilitate the isolation of nucleic acids from the maternal plasma sample, and amplification of markers to detect the allele frequency. The kit may also contain standard or control DNAs, such as DNA isolated from plasma of a mother pregnant with a healthy fetus, and/or DNA samples isolated from plasma samples from females carrying a fetuses with chromosomal abnormalities such as chromosome 21, 13, and/or 18 trisomy.

A kit for prenatal diagnosis of chromosomal abnormalities preferably comprises at least one methylation-sensitive enzyme, at least one pair of nucleic acid amplification primers capable of annealing and thus amplifying regions flanking sites that contain at least one polymorphic locus within differentially methylated regions in fetal and maternal DNA present in maternal plasma, at least one primer or probe to allow detection of alleles in the at least one polymorphic locus, and an instruction manual instructing the user to perform the steps of taking a plasma sample from a pregnant female, selectively digesting the nucleic acids present in said plasma sample with the methylation-sensitive enzyme to enrich the fetal nucleic acids in the sample, performing nucleic acid amplification using the amplification primers and detecting the alleles present in the sample enriched for the fetal nucleic acids, and interpreting the results so that if the ratio of two different alleles in the locus deviates from a control wherein the alleles are present in equal amounts, the fetus is affected with a chromosomal abnormality.

The kit may further comprise a control nucleic acid panel, wherein the controls comprise nucleic acids isolated from females pregnant with fetuses carrying known chromosomal abnormalities and females pregnant with fetuses without chromosomal abnormalities.

The kit may also further comprise an internal control of at least one pair of amplification primers and a detection primer or probe, wherein the primers and/or probe are selected from a nucleic acid region that is differentially methylated in fetal and maternal DNA present in maternal plasma, but that occur in chromosomes, wherein duplication or deletion is rare, so as to provide an internal control.

DETAILED DESCRIPTION OF THE INVENTION

The present invention provides methods for the detection of fetal chromosome abnormalities.

As used herein, the term "chromosomal abnormality" refers to a chromosome with DNA deletions or duplications and to chromosomal aneuploidy. The term also encompasses translocation of extra chromosomal sequences to other chromosomes.

As used herein, the term "chromosomal aneuploidy" refers to the abnormal presence (hyperploidy) or absence (hypoploidy) of a chromosome.

As used herein, the term "polymorphic marker" refers to segments of genomic DNA that exhibit heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), and the like. Polymorphic markers according to the present invention can be used to specifically differentiate between a maternal and paternal allele in the enriched fetal nucleic acid sample.

As used herein, the term "methyl-polymorphic marker" refers to a polymorphic marker that is adjacent to differentially methylated DNA regions of fetal and maternal DNA. The term adjacent refers to a marker that is within 1-3000 base pairs, preferably 1000 base pairs, more preferably 100 base pairs, still more preferably 50 base pairs from a differentially methylated nucleotide.

As used herein, the term "maternal allele frequency" refers to the ratio, represented as a percent, of a maternal allele to the total amount of alleles present (both paternal and maternal). The term "paternal allele frequency" refers to the ratio, represented as a percent, of a paternal allele to the total amount of alleles present (both paternal and maternal).

As used herein, the term "control DNA sample" or "standard DNA sample" refers to genomic DNA obtained from a healthy individual who does not have a chromosomal abnormality. Preferably, a control DNA sample is obtained from plasma of a female carrying a healthy fetus who does not have a chromosomal abnormality. Preferably, one uses a panel of control samples. Where certain chromosome anomalies are known one can also have standards that are indicative of a specific disease or condition. Thus, for example, to screen for three different chromosomal aneuploidies in a maternal plasma of a pregnant female, one preferably uses a panel of control DNAs that have been isolated from plasma of mothers who are known to carry a fetus with, for example, chromosome 13, 18, or 21 trisomy, and a mother who is pregnant with a fetus who does not have a chromosomal abnormality.

The present invention describes a non-invasive approach for diagnosing chromosomal abnormalities that uses fetal DNA obtained from maternal plasma. Fetal DNA comprises approximately 2-6% of the total DNA in maternal plasma in early and late pregnancy. Theoretically, in a normal fetus, half of the fetal DNA is contributed by the paternally-inherited fraction.

The present method can be used at any time once pregnancy occurs. Preferably, samples are obtained six weeks or more after conception. Preferably between 6 and 12 weeks after conception.

The technical challenge posed by analysis of fetal DNA in maternal plasma lies in the need to be able to discriminate the fetal DNA from the co-existing background maternal DNA. The methods of the present invention exploit such differences, for example, the differential methylation that is observed between fetal and maternal DNA, as a means to enrich for the relatively small percentage of fetal DNA present in a plasma DNA sample from the mother. The non-invasive nature of the approach provides a major advantage over conventional methods of prenatal diagnosis such as, amniocentesis, chronic vullus sampling and cordocentesis, which are associated with a small but finite risk of fetal loss. Also, because the method is not dependent on fetal cells being in any particular cell phase, the method provides a rapid detection means to determine the presence and also the nature of the chromosomal abnormality.

DNA isolation from blood, plasma, or serum of the pregnant mother can be performed using any method known to one skilled in the art. Standard methods of DNA isolation are described, for example, in (Sambrook et al., *Molecular Biol-*

*ogy: A laboratory Approach*, Cold Spring Harbor, N.Y. 1989; Ausubel, et al., *Current protocols in Molecular Biology*, Greene Publishing, Y, 1995). A preferred method for isolation of plasma DNA is described in Chiu et al., 2001, Clin. Chem. 47:1607-1613, which is herein incorporated by reference in its entirety. Other suitable methods include, for example TRI REAGENT® BD (Molecular Research Center, Inc., Cincinnati, Ohio), which is a reagent for isolation of DNA from, for example, plasma. TRI REAGENT BD and the single-step method are described, for example, in the U.S. Pat. Nos. 4,843,155 and 5,346,994.

According to the methods of the present invention, fetal DNA can be enriched in a plasma DNA sample that is obtained from an expecting mother by digesting the plasma DNA with one or more enzymes that selectively cleave part of the maternal DNA. For example, digesting plasma DNA with an enzyme that cleaves only at a DNA recognition site that is methylated or by digesting with an enzyme that cleaves only at a DNA recognition site that is unmethylated. Digesting with an enzyme that cleaves only an unmethylated DNA recognition site will enrich for DNA sequences that are methylated in fetal DNA but are not methylated in maternal DNA. Alternatively, digesting with an enzyme that cleaves only a methylated DNA recognition site will enrich for DNA sequences that are unmethylated in fetal DNA but are methylated in maternal DNA. Any enzyme that is capable of selectively cleaving maternal DNA regions and not the corresponding fetal DNA regions is useful in the present invention.

For example, a CG (or CpG) island is a short stretch if DNA in which the frequency of the CG sequence is higher than other regions. CpG islands are frequently found in the promoter regions of genes. Most CpG islands are more methylated when the gene is inactive and become less methylated or unmethylated, when the gene is active, i.e. translated. Thus, the methylation pattern is different in different cell types and varies during development. Since fetal DNA and maternal DNA are likely from different cell types and from different developmental stage, the regions of differential methylation can be easily identified and used to enrich the relative amount of fetal DNA in the maternal plasma sample.

As used herein, "methyl-sensitive" enzymes are DNA restriction endonucleases that are dependent on the methylation state of their DNA recognition site for activity. For example, there are methyl-sensitive enzymes that cleave at their DNA recognition sequence only if it is not methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated. As used herein, the terms "cleave", "cut" and "digest" are used interchangeably.

Methyl-sensitive enzymes that digest unmethylated DNA suitable for use in methods of the invention include, but are not limited to, HpaII, HhaI, MaeII, BstUI and AciI. A preferred enzyme of use is HpaII that cuts only the unmethylated sequence CCGG. Combinations of two or more methyl-sensitive enzymes that digest only unmethylated DNA can also be used. Suitable enzymes that digest only methylated DNA include, but are not limited to, DpnI, which cuts at a recognition sequence GATC, and McrBC, which belongs to the family of AAA$^+$ proteins and cuts DNA containing modified cytosines and cuts at recognition site 5' . . . Pu$^m$C(N$_{40-3000}$) Pu$^m$C . . . 3' (New England BioLabs, Inc., Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al., *Molecular Biology: A laboratory Approach*, Cold Spring Harbor, N.Y. 1989) provide a general description of methods for using restriction enzymes and other enzymes. In the methods of the present invention it is preferred that the enzymes are used under conditions that will enable cleavage of the maternal DNA with about 95%-100% efficiency, preferably with about 98%-100% efficiency.

Identification of Methyl-polymorphic Probes or Markers that Detect Different Alleles in Differentially Methylated DNA Regions The present invention exploits differences in fetal and maternal DNA as a means to enrich for fetal DNA present in a maternal plasma sample.

In one embodiment, the invention exploits differential methylation. In mammalian cells, methylation plays an important role in gene expression. For example, genes (usually, promoter and first exon regions) are frequently not methylated in cells where the genes are expressed, and are methylated in cells where the genes are not expressed. Since fetal DNA and maternal DNA in maternal plasma samples are often from different cell types, and/or of different developmental stages, regions of differential methylation can be identified. DNA fragments which represent regions of differential methylation are then sequenced and screened for the presence of polymorphic markers, which can be used as "labels" for maternal or paternal allelic DNA. Polymorphic markers located in specific genomic regions can be found in public databases, such as NCBI, or discovered by sequencing the differentially methylated genomic regions. The identified methyl-polymorphic markers can then be used as a diagnostic marker of chromosomal abnormalities by assessing the maternal or paternal allele frequency in the maternal plasma sample, wherein the fetal DNA has been enriched according to the methods of the present invention. The presence of a ratio other than about ½ of either maternal or paternal allele is indicative of either a duplication or a deletion of the particular chromosomal region wherein the polymorphic marker is located.

Regions of differential methylation can be identified by any means known in the art and probes and/or primers corresponding to those regions can be accordingly prepared. Various methods for identifying regions of differential methylation are described in, for example, U.S. Pat. Nos. 5,871,917; 5,436,142; and U.S. Patent Application Nos. US20020155451A1, US20030022215A1, and US20030099997, the contents of which are herein incorporated by reference in their entirety.

Isolation of fetal nucleic acids for the initial purpose of identifying differentially methylated regions in different fetal cells and in different fetal developmental stages can be performed from samples obtained from chorionic villus samples, amniotic fluid samples, or aborted fetuses using methods of nucleic acid isolation well known to one skilled in the art.

Examples of how to identify regions of that are differentially methylated in fetal DNA as compared to maternal DNA follow.

One exemplary method is described in U.S. Pat. No. 5,871,917. The method detects differential methylation at CpNpG sequences by cutting a test DNA (e.g., fetal DNA) and a control DNA (e.g., maternal DNA) with a CNG specific restriction enzyme that does not cut methylated DNA. The method uses one or more rounds of DNA amplification coupled with subtractive hybridization to identify differentially methylated or mutated segments of DNA. Thus, the method can selectively identify regions of the fetal genome that are hypo- or hypermethylated. It is in those regions, one can then easily identify any polymorphisms, such as SNPs, STRs, or RFLPs, which can be used to detect the allele frequency of the maternal and paternal alleles in the maternal plasma sample wherein fetal DNA is enriched.

In particular, maternal DNA is isolated and compared to DNA isolated from a fetus. The maternal and fetal DNA samples are separately cleaved by a methyl-sensitive enzyme that cleaves only at CNG sites that are unmethylated. The samples are further cleaved with a second enzyme that cleaves the DNA into a size and complexity appropriate for DNA amplification and subtractive hybridization. Preferably, the second enzyme cleaves DNA to produce ends that are neither homologous nor complimentary to a sticky-end produced by the methyl-sensitive enzyme. After cleavage, a set of adaptors is ligated onto the sticky-ends produced by the CNG specific restriction enzyme that does not cut methylated DNA. The adaptors are selected so that they will ligate to the CG-rich-ends of the DNA cut by the methyl-sensitive enzyme but not to the ends of the fragments that were cut with the second enzyme. The adaptors are chosen not only to ligate to DNA-ends cut by the methyl-sensitive enzyme, but also to be a good size and DNA sequence to act as a recognition site for primers to be used in DNA amplification. Only those fragments that have the adaptor and thus were cut with the methyl-sensitive enzyme will be amplified in a PCR reaction using adaptor sequence primers.

The two samples are separately amplified. After amplification, the first set of adaptors are removed from the ends of the amplified fragments by cleavage with the methyl-sensitive enzyme. This preserves the original ends of the fragments.

A second set of adaptors are ligated to the amplified maternal DNA, but not the amplified fetal DNA. The second set of adaptors is selected so that they do not have the same sequence as the first set of adaptors and so that they ligate only to DNA-ends cut by the methyl-sensitive enzyme. The second set of adaptors also provides a good recognition site for primers which are used for amplification.

At least one round of subtraction/hybridization followed DNA amplification is performed by standard methods. The result is a selection of DNA fragments that are uniquely unmethylated in maternal DNA, which can be used as probes to detect identified sites of methylation in the fetal genome.

In particular, the maternal DNA is mixed with a large excess of fetal DNA as described in U.S. Pat. No. 5,871,917. The subtraction hybridization mixture is then amplified by in vitro DNA amplification procedures using primers that hybridize to the second adaptor-ends. Thus, only maternal DNA fragments with second adaptor ends are amplified. Any maternal DNA that is hybridized to fetal DNA will not be amplified. A large excess of maternal DNA is used to promote formation of hybrids that are commonly found in both the fetal and maternal samples. The result is isolation of umethylated maternal DNA fragments that are uniquely methylated in fetal DNA. Fragments are isolated by standard methods known in the art.

A Southern Blot Hybridization can be performed to confirm that the isolated fragments detect regions of differential methylation. Maternal and fetal genomic DNA can be cut with a methyl-sensitive enzyme and hypometylation or hypermethylation at a specific site can be detected by observing whether the size or intensity of a DNA fragment cut with the restriction enzymes is the same between samples. This can be done by electrophoresis analysis and hybridizing the probe to the maternal and fetal DNA samples and observing whether the two hybridization complexes are the same or different sizes and/or intensities. Detailed methodology for gel electrophoretic and nucleic acid hybridization techniques are well known to one skilled in the art and protocols can be found, for example, in Sambrook et al., *Molecular Biology: A laboratory Approach*, Cold Spring Harbor, N.Y. 1989.

The fragment sequences can then be screened for polymorphic markers that can be used to differentiate between paternal or maternal alleles, which can be used as methyl-polymorphic probes as described herein. Probes isolated by the technique described above have at least 14 nucleotides to about 200 nucleotides.

Examples of suitable restriction enzymes for use in the above method include, but are not limited to BsiSI, Hin2I, MseI, Sau3A, RsaI, TspEI, MaeI, NiaIII, DpnI and the like. A preferred methyl-sensitive enzyme is Hpa II that recognizes and cleaves at nonmethylated CCGG sequences but not at CCGG sequences where the outer cytosine is methylated.

Differential methylation can also be assessed by the methods described in U.S. Patent Application No. 2003009997, which discloses a method for detecting the presence of differential methylation between two sources of DNA using enzymes that degrade either unmethylated or methylated DNA. For example, genomic maternal DNA can be treated with a mixture of methyl-sensitive enzymes that cleave only unmethylated DNA, such as HpaII, HhaI, MaeI, BstUI, and AciI so as to degrade unmethylated DNA. Genomic fetal DNA can then be treated with an enzyme that degrades methylated DNA, such as McrBC (New England Biolabs, Inc.). Subtractive hybridization then permits selective extraction of sequences that are differentially methylated between fetal and maternal DNA.

Alternatively, differential methylation between maternal and fetal DNA can be assessed by bisulfide treatment followed by either 1) sequencing, or 2) base-specific cleavage followed by mass spectrometric analysis as described in von Wintzingerode et al., 2002, PNAS, 99:7039-44, herein incorporated by reference in its entirety.

To serve as a probe, the identified methyl-polymorphic markers can be labeled by any procedure known in the art, for example by incorporation of nucleotides linked to a "reporter molecule".

A "reporter molecule", as used herein, is a molecule which provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin, or radioisotopes. Commonly used enzymes include horseradish peroxidase, alkaline phosphatase, glucose oxidase and beta-galactosidase, among others. Enzymes can be conjugated to avidin or streptavidin for use with a biotinylated probe. Similarly, probes can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicylic acid or tolidine are commonly used. Incorporation of a reporter molecule into a DNA probe can be by any method known to the skilled artisan, for example by nick translation, primer extension, random oligo priming, by 3' or 5' end labeling or by other means (see, for example, Sambrook et al. *Molecular Biology: A laboratory Approach*, Cold Spring Harbor, N.Y. 1989).

Alternatively, the identified methyl-polymorphic markers need not be labeled and can be used to quantitate allelic frequency using a mass spectrometry technique described in Ding C. and Cantor C. R., 2003, Proc. Natl. Acad. Sci. U.S.A. 100, 3059-64, which is herein incorporated by reference in its entirety.

Comparing Maternal and Paternal Allele Frequency

To diagnose the presence of a chromosomal abnormality using maternal plasma DNA according to the methods of the present invention, the plasma DNA can be first enriched for fetal DNA by digestion of plasma DNA with enzymes that selectively cleave maternal DNA, for example by using enzymes sensitive to the methylation state of the DNA. Polymorphic markers, such as the methyl-polymorphic markers described herein which are adjacent to or within differentially methylated fetal DNA regions, can be used to determine the allele frequency of either a paternal or a maternal allele. The allele frequency is compared to the allele frequency present in a control DNA sample (e.g. a genomic DNA obtained from an individual that does not have a chromosomal abnormality). Preferably, the control DNA is isolated from the plasma of a female pregnant with a healthy fetus.

A difference in allele frequency is indicative that a chromosomal abnormality is present in fetal DNA. Thus, in a normal sample, wherein substantially all of the maternal DNA has been digested, a ratio of maternal and paternal allele in any given locus is about ½ or 50% of the alleles present are of maternal and 50% of paternal origin. If any locus is either duplicated or deleted because of partial or complete chromosome duplication or deletion of a region wherein the particular allele is present, the ratio will differ from the 50%:50% ratio. The chromosomal abnormality can be a DNA deletion or duplication that includes the DNA sequence detected by the polymorphic probe. The deletion or duplication can be the result of chromosome aneuploidy (the presence or absence of an entire chromosome) or it can be the result of deletion or duplication within a chromosome. Chromosomal aneuploidy can be confirmed by any method known to those skilled in the art. A preferred method for conformation of chromosomal aneuploidy is amniocentesis followed by fluorescence in situ hybridization (FISH), by traditional karyotyping with Geisma-staining or by spectral karyotyping (SKY), which are all methods well known to one skilled in the art.

Any polymorphic marker located in the region with, for example the differential methylation status between maternal and fetal DNA, or any other, preferably epigenetic information difference, between the maternal and fetal DNA, can be used to detect the frequency of the maternal and paternal allele in the fetal DNA present in the maternal plasma. Thus, once the differentially methylated regions have been determined, a skilled artisan can easily turn to databases, wherein one, and preferably more than one, SNPs or other polymorphic markers can be picked that are located within the differentially methylated DNA regions. Alternatively, sequencing the region from several individuals can reveal new useful nucleic acid polymorphisms.

Methods for determining allele frequency are well known to those skilled in the art. The allelic frequency using the polymorphic probes that detect differential DNA regions, can be determined by any such method. For example, a quantifiable label can be incorporated into methyl-polymorphic probes that specifically detect either maternal of paternal DNA. The probes are then hybridized to the DNA sample, e.g., by Southern Blot, and quantitated. Preferred labels for such a method are radioisotopes and fluorescent markers that can be quantitated by densitometry.

After digestion of the maternal nucleic acids in the plasma sample, the maternal and paternal alleles present in the enriched fetal nucleic acid sample are preferably amplified using PCR. The allele ratio is then measured using various differential amplification methods described below, including different primer extension methods. Preferably, the analysis is performed using a primer-extension reaction after a polymerase chain reaction (PCR) and detecting the primer extension products using mass spectrometry. One preferred method of the present invention for determination of allelic frequency using mass spectrometry technique is described in Ding C. and Cantor C. R., 2003, Proc. Natl. Acad. Sci. U.S.A. 100, 3059-64. The MassARRAY system is based on matrix-assisted laser desorption ionization/time-of-flight (MALDI-TOF) mass spectrometric (MS) analysis of primer-extension products (Tang, K. et al. *Proc Natl Acad Sci USA* 96, 10016-10020 (1999)).

Alternatively, the detection can be performed using, for example, electrophoretic methods including capillary electrophoresis, using denaturing high performance liquid chromatography (D-HPLC), using an Invader® Assay (Third Wave Technologies, Inc., Madison, Wis.), pyrosequencing techniques (Pyrosequencing, Inc., Westborough, Mass.) or solid-phase minisequencing (U.S. Pat. No. 6,013,431; Suomalainen et al. Mol. Biotechnol. June; 15(2):123-31, 2000).

The allele frequency is presented as the ratio of either a maternal allele and a paternal allele in the total amount of alleles present (both paternal and maternal). Since the allelic frequency is a ratio, the maternal or paternal allele frequency of the control DNA sample can be determined using either different or the same probes used to detect the allele frequency in fetal DNA.

Preferably, two, three, four, 5-10 or even more than 10 polymorphic loci can be analyzed in the same reaction. Using a pool of several polymorphic markers allows one to perform the analysis even if the parental alleles are not known and still allow identification of at least one informative marker, i.e., loci wherein the two alleles in the fetal sample are different, i.e. the allele inherited from the father is different than the allele inherited from the mother. Preferably, the markers are selected in different locations along the desired chromosomes, such as chromosomes 21, 13, and 18.

Alternatively, one can first determine the informative loci by genotyping the maternal and paternal loci using a selected polymorphic markers in the chromosomal regions that are differentially methylated in the maternal and fetal DNA, and use only a selection of those markers, wherein the alleles differ, in determining the allele frequency in the fetal DNA sample.

Herein, a difference in allelic frequency of either maternal or paternal alleles refers to a difference that is at least 3%, preferably at least 10%, and more preferably at least 15%. Preferably, the normal allele ratio of maternal and paternal alleles in the plasma DNA sample, wherein the maternal DNA has been substantially completely digested is 50% of maternal allele and 50% of paternal allele. If this allelic ratio changes for any give locus, the fetus is likely to carry a duplication or deletion of the chromosomal region, wherein the allele is located.

In one embodiment of the invention, an amplification step is performed to further enrich for fetal DNA in a sample of maternal plasma. Amplification is performed after the enrichment of fetal DNA in plasma DNA by enzymatic digestion and prior to the detection of allelic frequency/ratio. Amplification can be performed by any method known in the art (such as, Polymerase Chain Reaction (PCR) or rolling circle amplification) using primers that anneal to the selected fetal DNA regions. Oligonucleotide primers are selected such that they anneal to the sequence to be amplified. Preferably, the amplification is performed using the rolling circle method which allows combining the amplification reaction with an enzymatic methylation step, wherein the methylation status of the fetal and/or the remaining maternal DNA is preserved through the amplification. Preferably, the amplification step is followed by another enzymatic digestion step to further remove any remaining maternal DNA from the sample.

Oligonucleotide primers for PCT, rolling circle amplification and primer extension reactions described herein, may be synthesized using methods well known in the art, including, for example, the phosphotriester (see Narang, S. A., et al., 1979, Meth. Enzymol., 68:90; and U.S. Pat. No. 4,356,270), phosphodiester (Brown, et al., 1979, Meth. Enzymol., 68:109), and phosphoramidite (Beaucage, 1993, Meth. Mol. Biol., 20:33) approaches. Each of these references is incorporated herein in its entirety by reference.

Alternatively, one may mask the maternal DNA and/or selectively amplify the fetal DNA to accentuate the amount of fetal DNA in the sample and allow detection of allele ratio in the fetal DNA.

In one aspect, the invention provides a method for prenatal diagnosis of chromosomal abnormality in a fetus. The method comprises the steps of a) obtaining a plasma/blood/serum sample from a pregnant female and isolating DNA from said sample, b) digesting isolated DNA with a methyl-sensitive enzyme that digests only unmethylated DNA, c) isolating undigested DNA from step b), d) amplifying the undigested DNA from step c) while simultaneously using a DNA methylase to methylate nascent hemi-methylated DNA, e) digesting amplified DNA of step d) with a methyl-sensitive enzyme that digests only unmethylated DNA, f) determining the paternal or maternal allele frequency using polymorphic markers adjacent to unmethylated fetal DNA regions; and, g) comparing the paternal or maternal allele frequency or ratio of step f) to a control DNA sample, wherein a difference in allele frequency is indicative of a chromosomal abnormality in the fetus.

The first digestion of the maternal DNA sample enriches for fetal DNA that is methylated. The amplification step provides for additional enrichment of fetal DNA by amplifying and further maintaining the methylation status of fetal DNA.

The amplification step is combined with the use of a DNA methylase that is specific for hemi-methylated DNA (such as, Dnmt1) in order to methylate nascent hemi-methylated DNA. Since fetal DNA that is methylated is enriched in the first digestion, the methylase will only methylate fetal DNA and not maternal DNA in the amplification process. During amplification, methylated fetal DNA and any background unmethylated maternal DNA are produced. Therefore, the amplified DNA sample is again digested with a methyl-sensitive enzyme that digests only unmethylated DNA. Such an amplification procedure provides a second stage of fetal DNA enrichment.

In a preferred embodiment, rolling circle amplification (RCA) is used. Rolling circle amplification is an isothermal process for generating multiple copies of a sequence. In rolling circle DNA replication in vivo, a DNA polymerase extends a primer on a circular template (Komberg, A. and Baker, T. A. DNA Replication, W.H. Freeman, New York, 1991). The product consists of tandemly linked copies of the complementary sequence of the template. RCA is a method that has been adapted for use in vitro for DNA amplification (Fire, A. and Si-Qun Xu, Proc. Natl. Acad. Sci. USA, 1995, 92:4641-4645; Lui, D., et al., J. Am. Chem. Soc., 1996, 118:1587-1594; Lizardi, P. M., et al., Nature Genetics, 1998, 19:225-232; U.S. Pat. No. 5,714,320 to Kool). RCA techniques are well known in the art, including linear RCA (LRCA). Any such RCA technique can be used in the present invention.

The methods of the present invention are suitable for diagnosing a chromosomal abnormality in a fetus, e.g., detecting chromosomal deletions, duplications and/or aneuploidy.

The advantage of the methods described herein, is that chromosomal abnormalities can be detected using plasma/blood/serum DNA from the mother, which contains only a small percent of fetal cells and hence, a small percentage of fetal DNA. The present invention provides methods for the enrichment of fetal DNA through the specific digestion of maternal DNA and provides an easy non-invasive approach to obtaining fetal DNA samples that can be used to screen for chromosomal abnormalities in fetuses carried by pregnant females.

Moreover, because the method does not rely on visual inspection of chromosomes, the need to grow fetal cells and/or synchronize the cell cycle of the fetal cells is not needed thus allowing rapid screening in the time sensitive prenatal diagnosis.

The methods are particularly useful for, but not limited to, diagnosing chromosomal aneuploidies such as Down's syndrome, Turner's syndrome, trisomy 13, trisomy 18, and Klinefelter syndrome.

Down's syndrome is characterized by the presence of 3 copies chromosome 21 instead of one, and is often referred to as trisomy 21. Three to four percent of all cases of trisomy 21 are due to Robertsonian Translocation. In this case, two breaks occur in separate chromosomes, usually the 14th and 21st chromosomes. There is rearrangement of the genetic material so that some of the 14th chromosome is replaced by extra 21st chromosome. So while the number of chromosomes remain normal, there is a triplication of the 21st chromosome material. Some of these children may only have triplication of part of the 21st chromosome instead of the whole chromosome, which is called a partial trisomy 21. The extra DNA produces the physical and mental characteristics of Down syndrome, which include a small head that is flattened in the back; slanted eyes; extra skin folds at the corners of the eyes; small ears, nose and mouth; short stature; small hands and feet; and some degree of mental disability.

Trisomy 13 and 18 refer to an extra chromosome 13 or 18, respectively. Trisomy 13, also known as Patua's syndrome, is characterized by a small at birth weight. Spells of interrupted breathing (apnea) in early infancy are frequent, and mental retardation is usually severe. Many affected children appear to be deaf. A moderately small head (microcephaly) with sloping forehead, wide joints and openings between parietal bones of the head are present. Gross anatomic defects of the brain, especially failure of the forebrain to divide properly (holoprosencephaly) are common. A hernial protrusion of the cord and its meninges through a defect in the vertebral canal (myelomeningocele) is found in almost 50% of cases.

The entire eye is usually small (microphthalmia), and a defect of the iris tissue (coloboma), and faulty development of the retina (retinal dysplasia) occur frequently. The supraorbital ridges are shallow and palapebral fissures are usually slanted. Cleft lip, cleft palate, or both are present in most cases. The ears are abnormally shaped and unusually low-set.

Trisomy 18, or Edwards syndrome, results in babies that appear thin and frail. They fail to thrive and have problems feeding. Trisomy 18 causes a small head size, with the back of the head (occiput) prominent. Ears are usually low set on the head. The mouth and jaw are unusually small, and there is a shortened sternum (breastbone). At birth, these babies are small for their age, even when delivered full-term, and have a weak cry. Their response to sound is decreased and there is often a history of infrequent fetal activity during the pregnancy. About 90 percent of babies with trisomy 18 have heart defects. They clench their fists in a characteristic manner and extending the fingers fully is difficult. Joint contractures, where the arms and legs are in a bent position rather than relaxed, are usually present. The feet may be referred to as "rocker bottom" due to their shape. Babies with trisomy 18 may also have spinal bifida (in 6 percent of cases), eye problems (in 10 percent of cases), cleft lip and palate (in most cases), and hearing loss (in most cases). It is also common to see feeding problems, slow growth, seizures (about 30 percent of cases in the first year), high blood pressure, kidney problems and scoliosis (curvature of the spine). In males, the testes fail to descend into the scrotum.

Turner syndrome, or monosomy X, is usually caused by a missing X chromosome. It affects 1 out of 3,000 live births. The main features of the syndrome are short stature, webbing of the skin of the neck, absent or retarded development of secondary sexual characteristics, absence of menstruation, coarctation (narrowing) of the aorta, and abnormalities of the eyes and bones. The condition is usually either diagnosed at birth because of the associated anomalies, or at puberty when there is absent or delayed menses and delayed development of normal secondary sexual characteristics. The methods described herein enable pre-birth diagnosis.

Klinefelter syndrome refers to males that have an extra sex chromosome, XXY instead of the usual male arrangement, XY. The syndrome is characterized by men who had enlarged breasts, sparse facial and body hair, small testes, and an inability to produce sperm. Although they are not mentally retarded, most XXY males also have some degree of language impairment.

The methods of the present invention, provide for a non-invasive approach for diagnosis of chromosomal abnormalities and related syndromes.

The invention will now be further illustrated with reference to the following examples. It will be appreciated that what follows is by way of example only and that modifications to detail may be made while still falling within the scope of the invention.

EXAMPLES

The following is an example that illustrates the steps for diagnosis of Down's syndrome using maternal plasma DNA. The approach is applicable for any chromosomal aneuploidy or chromosomal DNA duplication.

In Down's syndrome, the fetus has three chromosomes 21. In 90% of the cases of trisomy 21, the fetus obtained two chromosomes 21 from the mother and one chromosome 21 from the father. The detection of extra chromosome 21 DNA is performed as follows:

DNA regions in chromosome 21 are screened for differential methylation—methylated in fetal DNA and not methylated in maternal DNA (mostly peripheral blood cells).

Polymorphic markers that are close to the differentially methylated DNA regions that can be used as labels for maternal and paternal DNA are identified.

A plasma sample is obtained from a pregnant female and DNA is isolated from the sample.

The isolated plasma DNA is treated with a methylation sensitive enzyme (e.g. Hpa II) that cuts only the unmethylated DNA sequence CCGG. The Enzyme is used to digest unmethylated maternal DNA, leaving only methylated fetal DNA fragments. Alternatively, an enzyme that cuts only methylated DNA (such as Dpn I, which recognizes the sequence GATC) can also be used, the following steps are adjusted accordingly.

A substantial difference between the paternal allele frequency in trisomy 21 and the paternal allele frequency for a normal individual (table below) will be observed. In the table, allele A is maternal specific and allele B is paternal specific.

In the table below, the paternal allele frequency less than the control is indicative of Down's syndrome.

|  | Maternal DNA | Fetal DNA | Paternal Allele frequency |
|---|---|---|---|
| Trisomy 21 | AA | AAB | 1/3 or 33.3% |
| Control sample | AA | AB | 1/2 or 50% |

Confirmation that the chromosomal abnormality is due to chromosomal aneuploidy represented by an extra chromosome 21 can be confirmed by means known in the art, such as amniocentesis.

If the enzymatic digestion is less than 100% efficient, a difference in allele frequency will still be observed but instead of a 16.7% difference (as illustrated in table), the difference observed may be in the range of 5-10%, and it is thus preferable, that a control locus (C/D alleles in the normal, or non-aneuploidy locus in the table below) is used to provide a control. This is illustrated in the following table:

|  | Maternal DNA | Fetal DNA | B (or D) % 100 digestion | B (or D) % 98% digestion |
|---|---|---|---|---|
| Trisomy 21 | AA | AAB | 33.3% | 20% |
| Non-aneuploidy | CC | CD | 50% | 25% |

In the case that there is not 100% digestion, an additional amplification scheme can also be incorporated in to the method described above in order to further enrich for fetal DNA. Assuming a DNA region that is methylated in fetal DNA and not methylated in maternal DNA is used.

The majority of maternal DNA will be digested using a methylation sensitive enzyme as described above. This is the first step of fetal DNA enrichment.

Both maternal and fetal DNA will then be amplified by an isothermal mechanism (such as rolling circle amplification). Simultaneously, a DNA methylase (such as Dnmt1) specific for hemi-methylated DNA is used to methylate nascent hemi-methylated DNA. Since only the fetal DNA is methylated at the beginning, the methylase will only methylate fetal DNA in the amplification process. As a result, methylated fetal DNA and unmethylated DNA are produced.

The amplified sample will then be digested again using a methylation sensitive enzyme that will digest the unmethylated maternal DNA (e.g. HpaII). This is the second step of fetal DNA enrichment. After this step, vast majority of DNA left is fetal DNA. For future DNA quantifications, this is equivalent to 100% Hpa II digestion.

All references described herein are incorporated herein by reference.

We claim:

1. A method for prenatal diagnosis of chromosomal abnormality in a predetermined DNA region comprising the steps of: a) obtaining a plasma sample from a pregnant female; b) enriching fetal DNA regions in the plasma sample by digesting DNA from said plasma sample with a methyl-sensitive enzyme that selectively and substantially completely digests the maternal DNA to obtain a sample enriched for fetal DNA regions; and c) determining the paternal and maternal allele frequency in the sample enriched for fetal DNA using polymorphic markers adjacent to or within the fetal DNA regions in the sample enriched for the fetal DNA regions of step (b), wherein a difference in allele frequency from other than 50% of paternal and 50% of maternal allele as compared to a normal control, which does not comprise a chromosomal abnormality is indicative of a chromosomal abnormality.

2. The method of claim 1, wherein the DNA is isolated from the plasma sample before it is digested.

3. The method of claim 1, wherein comparing the paternal or maternal allele frequency of step (c) is performed against at least one internal control located in a chromosome, duplication or deletion of which is not a target of diagnosis, and wherein both maternal and paternal alleles are present in equal amount, wherein deviation of the ratio from the internal control indicates presence of chromosomal abnormality.

4. The method of claim 1 further comprising a DNA amplification step performed after step (a) and before step (c).

5. The method of claim 1, wherein said methyl-sensitive enzyme digests only at DNA recognition sites that are unmethylated and wherein the maternal or paternal allele, frequency is determined using polymorphic markers adjacent to or within methylated fetal DNA regions.

6. The method of claim 3, wherein said methyl-sensitive enzyme digests only at DNA recognition sites that are methylated, and wherein the maternal or paternal allele frequency is determined using polymorphic markers adjacent to or within unmethylated fetal DNA regions.

7. A method for prenatal diagnosis of chromosomal abnormality comprising the steps of: a) obtaining a plasma sample from a pregnant female; b) enriching fetal DNA regions in the plasma sample by digesting DNA present in said plasma sample with a methyl-sensitive enzyme that digests only unmethylated DNA; c) optionally isolating undigested enriched fetal DNA regions from step (b); d) amplifying the undigested enriched fetal DNA regions from step (b) or (c) while using a DNA methylase to methylate nascent hemimethylated DNA; e) digesting the amplified DNA of step (d) with a methyl-sensitive enzyme that digests only unmethylated DNA; and f) determining the paternal or maternal allele frequency in the enriched fetal DNA regions using polymorphic markers adjacent to or within unmethylated fetal DNA regions, wherein a difference in allele frequency other than 50% of maternal and 50% of paternal is indicative of a chromosomal abnormality.

8. The method of claim 7, wherein the comparing of the paternal or maternal allele frequency of step (f) is performed against a control DNA sample, wherein a difference of other than the ratio in the control sample is indicative of a chromosomal abnormality.

9. The method of claim 7, wherein the DNA is isolated from the plasma sample before it is digested.

10. The method of claim 1 or 7, wherein the chromosomal abnormality is DNA duplication.

11. The method of claim 1 or 7, wherein then chromosomal abnormality is a DNA deletion.

12. The method of claim 1 or 7, wherein the chromosomal abnormality is aneuploidy.

13. The method of claim 12, wherein said aneuploidy is selected from the group consisting of trisomy 21, trisomy 18, and trisomy 13.

* * * * *

UNITED STATES PATENT AND TRADEMARK OFFICE
CERTIFICATE OF CORRECTION

PATENT NO. : 7,655,399 B2  Page 1 of 1
APPLICATION NO. : 10/575119
DATED : February 2, 2010
INVENTOR(S) : Cantor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 110 days.

Signed and Sealed this

Twenty-third Day of November, 2010

David J. Kappos
*Director of the United States Patent and Trademark Office*